(12) United States Patent
Zadeh

(10) Patent No.: US 9,204,943 B1
(45) Date of Patent: Dec. 8, 2015

(54) COREFLEX ABUTMENT SYSTEM

(71) Applicant: Parsa T. Zadeh, Beverly Hills, CA (US)

(72) Inventor: Parsa T. Zadeh, Beverly Hills, CA (US)

( * ) Notice: Subject to any disclaimer, the term of this patent is extended or adjusted under 35 U.S.C. 154(b) by 0 days.

(21) Appl. No.: 13/752,171

(22) Filed: Jan. 28, 2013

(51) Int. Cl.
*A61C 8/00* (2006.01)
*A61K 6/04* (2006.01)

(52) U.S. Cl.
CPC ............ *A61C 8/0086* (2013.01); *A61C 8/006* (2013.01); *A61C 8/0016* (2013.01); *A61C 8/0057* (2013.01); *A61C 8/0069* (2013.01); *A61K 6/04* (2013.01)

(58) Field of Classification Search
CPC .... A61C 8/005; A61C 8/008; A61B 17/3468; B29C 65/48
USPC ................... 433/172–177, 191, 195, 201.1; 604/93.01; 623/1.11
See application file for complete search history.

(56) References Cited

U.S. PATENT DOCUMENTS

| | | | | |
|---|---|---|---|---|
| 2,414,415 A * | 1/1947 | Rhodes | ........................ | 156/335 |
| 3,314,420 A * | 4/1967 | Smith et al. | ................. | 623/23.3 |
| 3,955,280 A * | 5/1976 | Sneer | ............................ | 433/169 |
| 4,318,696 A | 3/1982 | Kasama et al. | | |
| 4,324,550 A * | 4/1982 | Reuther et al. | ................ | 433/174 |
| 4,439,152 A * | 3/1984 | Small | ............................ | 433/173 |
| 4,446,579 A * | 5/1984 | Inamori et al. | ............. | 623/11.11 |
| 4,657,510 A * | 4/1987 | Gittleman | .................... | 433/173 |
| 4,689,013 A * | 8/1987 | Lustig | ........................... | 433/181 |
| 4,872,840 A * | 10/1989 | Bori | ............................ | 433/173 |
| 4,957,437 A * | 9/1990 | Shimura et al. | ............... | 433/169 |
| 4,988,297 A * | 1/1991 | Lazzara et al. | ................ | 433/173 |
| 5,125,839 A * | 6/1992 | Ingber et al. | .................... | 433/169 |
| 5,174,755 A * | 12/1992 | Fukuda | .......................... | 433/173 |
| 5,234,339 A * | 8/1993 | Grigereit | ........................ | 433/172 |
| 5,417,570 A * | 5/1995 | Zuest et al. | ................... | 433/177 |
| 5,527,182 A | 6/1996 | Willoughby | | |
| 5,556,280 A * | 9/1996 | Pelak | ............................ | 433/172 |
| 5,749,731 A * | 5/1998 | Morgan et al. | ................ | 433/173 |
| 5,873,721 A | 2/1999 | Willoughby | | |
| 5,954,505 A | 9/1999 | Ford | | |
| 6,283,753 B1 | 9/2001 | Willoughby | | |
| 6,655,962 B1 * | 12/2003 | Kennard | ........................ | 433/174 |
| 6,840,770 B2 * | 1/2005 | McDevitt | ...................... | 433/173 |
| 6,939,135 B2 * | 9/2005 | Sapian | .......................... | 433/174 |
| 7,300,282 B2 * | 11/2007 | Sapian | ........................... | 433/173 |
| 7,309,231 B2 * | 12/2007 | Engman | ........................ | 433/173 |
| 7,682,152 B2 | 3/2010 | Ford et al. | | |
| 8,187,000 B2 * | 5/2012 | Schaub | ......................... | 433/173 |
| 2004/0209228 A1 | 10/2004 | Ilan | | |
| 2004/0234925 A1 * | 11/2004 | Benhamou | .................... | 433/173 |
| 2006/0154204 A1 * | 7/2006 | Reggie | ............................ | 433/173 |
| 2006/0154205 A1 * | 7/2006 | Reggie | ............................ | 433/173 |
| 2007/0092851 A1 * | 4/2007 | Engman | ......................... | 433/173 |
| 2007/0099151 A1 * | 5/2007 | Ilan et al. | ....................... | 433/173 |

(Continued)

FOREIGN PATENT DOCUMENTS

| | | |
|---|---|---|
| CN | 201026242 | 2/2008 |
| EP | 2.127.612 | 12/2009 |
| WO | WO 2004105632 A1 * | 12/2004 |

*Primary Examiner* — Cris L Rodriguez
*Assistant Examiner* — Mirayda A Aponte
(74) *Attorney, Agent, or Firm* — Michael I. Kroll

(57) ABSTRACT

The present invention relates to dental implants and provides a flexible core abutment system using an implantable base member, a flexible inner core and an outer shell for receiving a restoration wherein the flexibility of the abutment simulates the shock absorbing properties typically provided by the ligaments of natural teeth.

10 Claims, 9 Drawing Sheets

(56) References Cited

U.S. PATENT DOCUMENTS

| | | |
|---|---|---|
| 2007/0141532 A1* | 6/2007 | Ford et al. .................. 433/173 |
| 2008/0008981 A1* | 1/2008 | Groll et al. .................. 433/173 |
| 2008/0014555 A1* | 1/2008 | Cippiciani .................. 433/173 |
| 2009/0123888 A1* | 5/2009 | Rosenberg .................. 433/173 |
| 2010/0129774 A1* | 5/2010 | Martinez et al. .......... 433/201.1 |
| 2012/0129132 A1* | 5/2012 | Lomicka et al. ............. 433/173 |
| 2012/0264082 A1* | 10/2012 | Segura et al. ............... 433/174 |
| 2012/0315599 A1* | 12/2012 | Mullaly ...................... 433/173 |

* cited by examiner

COREFLEX ABUTMENT SYSTEM

BACKGROUND OF THE INVENTION

1. Field of the Invention

The present invention relates generally to independent dental endosteal implants and, more specifically, to an abutment assembly that provides flexibility to the restoration without compromising the integrity and biologic requirements of passing through soft tissue and attaching to the implant.

One disadvantage of the prior art is that the feel of masticating different food items is different on implants. Another is that the mastication seems louder to the patient. Furthermore, when seating the crowns and bridges, the slightest misfit will prevent complete seating due to the lack of any flexibility. Another disadvantage of the prior art is that when implants are used next to natural teeth, if they are at the level of the natural teeth, they feel high and in premature occlusion as soon as the teeth are subjected to occlusional forces.

The present invention seeks to overcome these drawbacks by presenting an abutment assembly having a flexible nylon core to provide versatility to the implantation and usage of restorations.

2. Description of the Prior Art

There are other implant devices designed for the oral cavity. Typical of these is U.S. Pat. No. 4,318,696 issued to Kasama et al. on Mar. 9, 1982.

Another patent was issued to Shimura et al. on Sep. 18, 1990 as U.S. Pat. No. 4,957,437. Yet another U.S. Pat. No. 5,174,755 was issued to Fukuda on Dec. 29, 1992 and still yet another was issued on Jun. 18, 1996 to Willoughby as U.S. Pat. No. 5,527,182.

Another patent was issued to Willoughby on Feb. 23, 1999 as U.S. Pat. No. 5,873,721. Yet another U.S. Pat. No. 5,954,505 was issued to Ford on Sep. 21, 1999. Another was issued to Willoughby on Sep. 4, 2001 as U.S. Pat. No. 6,283,753 and still yet another was published on Oct. 21, 2004 to Ilan as U.S. Patent Application No. 2004/0209228.

Another patent was issued to Sapian on Nov. 27, 2007 as U.S. Pat. No. 7,300,282. Yet another U.S. Pat. No. 7,682,152 was issued to Ford et al. on Mar. 23, 2010. Another application was published to Zhou on Feb. 27, 2008 as Chinese Patent Application Publication No. CN201026242 and still yet another application was published on Dec. 2, 2009 to Baruc as European Patent Application Publication No. EP2127612.

U.S. Pat. No. 4,318,696
Inventor: Katsumi Kasama et al.
Issued: Mar. 9, 1982

The present invention provides an implant artificial denture comprising an intra-ossal implant implanted in the jaw, an elastic material fitted over the head of the intra-ossal implant, a crown of tooth and, if required, a receiver fitted over the head of the intra-osseal implant, wherein the receiver prevents the elastic material from falling off when chewing and masticatory pressure or shock is applied thereto and the elastic material absorbs the chewing and masticatory pressure or shock applied thereto to prevent lesion of the surrounding tissue, and further provides an implant artificial denture equipped with a chewing load limit sensing device incorporated therein, which aids in preventing lesion of the surrounding tissue.

U.S. Pat. No. 4,957,437
Inventor: Kaizo Shimura et al.
Issued: Sep. 18, 1990

An artificial tooth comprises a contacting member formed of a composite material having compatibility with living tissues and disposed at an outer portion of the artificial tooth to be contacted with alveolar bone, a metal base member having an opening therein and disposed inside of and attached to the contacting member, a metal post inserted into the opening of the metal base member and at least two elastic buffer members disposed in a space between the metal base member and the metal post. The composite material having compatibility with living tissues contains 40 to 95% by weight of a calcium phosphate compound and 60 to 5% by weight of an organic polymer. Each of the elastic buffer members is spaced apart for movably receiving the metal post by which pressure imposed upon the artificial tooth is transmitted.

U.S. Pat. No. 5,174,755
Inventor: Hiroshi Fukuda
Issued: Dec. 29, 1992

A dental implant comprising an artificial root which is embedded in a jaw bone and a post to which an artificial tooth is attached, wherein a stress absorbing member made of a super elastic material is provided in at least a part of the implant between the artificial root and the post. Preferably, a stress absorbing system consisting of a super elastic material member and a polymeric material member is employed.

U.S. Pat. No. 5,527,182
Inventor: Andrew J. M. Willoughby
Issued: Jun. 18, 1996

Dental implant abutment systems, related devices, and implantology processes and techniques. The abutment systems include a base that is adapted to mount in nonrotating fashion on any desired dental implant, root form or blade, from any supplier, together with a fixation screw which secures the base to the implant. A core, to which an abutment is cast in customized shape and form as desired is attached to the base preferably in threaded fashion and secured with an appropriate antirotational mechanism. Alternatively, the core and abutment may be formed using CAM processes. Such abutment systems, unlike prevalent conventional systems, do not require a central access bore in the core or abutment components, and they occupy significantly less volume than conventional abutments. Accordingly, abutment systems according to the present invention more flexibly accommodate a wide range of axial inclinations between implant and the overlying crown or prosthesis, preclude loosening of fixation screws, allow precision attachments to be included in the abutments for providing virtually completely passively fitting patient removable prostheses, and save considerable time, effort and expense because of the added simplicity and lower parts inventory required. Also disclosed are tapered gingivectomy procedures for replicating natural tooth emergence which is enhanced by abutments according to the present invention, together with precision attachments, impression copings and analogs, and other peripheral components useful with systems and techniques of the present invention.

U.S. Pat. No. 5,873,721
Inventor: Andrew J. M. Willoughby
Issued: Feb. 23, 1999

Dental implant abutment systems, related devices, and implantology processes and techniques. The abutment systems include a base that is adapted to mount in non-rotating fashion on any desired dental implant, root form or blade, from any supplier, together with a fixation screw which secures the base to the implant. A core, to which an abutment is cast in customized shape and form as desired is attached to the base preferably in threaded fashion and secured with an appropriate anti-rotational mechanism. Alternatively, the core and abutment may be formed using CAM processes. Such abutment systems, unlike prevalent conventional systems, do not require a central access bore in the core or abutment components, and they occupy significantly less volume than conventional abutments. Accordingly, abutment systems according to the present invention more flexibly accommodate a wide range of axial inclinations between implant and the overlying crown or prosthesis, preclude loosening of fixation screws, allow precision attachments to be included in the abutments for providing virtually completely passively fitting patient removable prostheses, and save considerable time, effort and expense because of the added simplicity and lower parts inventory required. Also disclosed are tapered gingivectomy procedures for replicating natural tooth emergence which is enhanced by abutments according to the present invention, together with precision attachments, impression copings and analogs, and other peripheral components useful with systems and techniques of the present invention.

U.S. Pat. No. 5,954,505
Inventor: Christopher W. Ford
Issued: Sep. 21, 1999

The preferred embodiment consists primarily of an anchor for implantation into the patient's crestal bone or other suitable bony structure, an insert which is flexibly received within the anchor and would be mounted so as to allow modulation of forces being transferred from the insert to the anchor. The insert would also act as a platform for mounting the prosthetic or artificial tooth. The prosthesis allows elastic movement of the artificial tooth along three orthogonal axes.

U.S. Pat. No. 6,283,753
Inventor: Andrew J. M. Willoughby
Issued: Sep. 4, 2001

Dental implant abutment systems, related devices, and implantology processes and techniques. The abutment systems include a base that is adapted to mount in nonrotating fashion on any desired dental implant, root form or blade, from any supplier, together with a fixation screw which secures the base to the implant. A core, to which an abutment is cast in customized shape and form as desired is attached to the base preferably in threaded fashion and secured with an appropriate antirotational mechanism. Alternatively, the core and abutment may be formed using CAM processes. Such abutment systems, unlike prevalent conventional systems, do not require a central access bore in the core or abutment components, and they occupy significantly less volume than conventional abutments. Accordingly, abutment systems according to the present invention more flexibly accommodate a wide range of axial inclinations between implant and the overlying crown or prosthesis, preclude loosening of fixation screws, allow precision attachments to be included in the abutments for providing virtually completely passively fitting patient removable prostheses, and save considerable time, effort and expense because of the added simplicity and lower parts inventory required. Also disclosed are tapered gingivectomy procedures for replicating natural tooth emergence which is enhanced by abutments according to the present invention, together with precision attachments, impression copings and analogs, and other peripheral components useful with systems and techniques of the present invention.

U.S. Patent Number 2004/0209228
Inventor: Daniel Ilan
Published: Oct. 21, 2004

The present invention relates to a polymeric implant, especially useful for dental medicine. More specifically, the present invention relates to a polymerizable device comprising an artificial tooth's root and an abutment anchored therein and to a kit comprising interalia the same. The present invention also relates to a method for implanting said implant in the alveolar bore of previously extracted tooth.

U.S. Pat. No. 7,300,282
Inventor: Schubert L. Sapian
Issued: Nov. 27, 2007

A biofunctional dental implant wherein a crown portion is connected to a root portion without the use of the conventional short screws, or the like. A flexible abutment projects upwardly from the root portion, and the crown portion is positioned in surrounding engagement with the flexible abutment. A threaded abutment post is advanced through the flexible abutment and into receipt by the root portion. The advancement of the abutment post through the flexible abutment generates an outward pushing force for causing a plurality of flexible splines of the abutment to bend outwardly and into engagement with an elastomeric cap of the crown portion for holding the crown portion atop the root portion. In one preferred embodiment, a replacement crown portion is detachably connected to an existing root portion by way of a removable abutment screw so as to enable a broken or worn crown portion to be removed and replaced without the need for a new surgery.

U.S. Pat. No. 7,682,152
Inventor: Christopher W. Ford
Issued: Mar. 23, 2010

A dental implant assembly (20) including a core body (40, 140, 240, 340, 440) for engaging a tooth-replicating device (52). The core body (40, 140, 240, 340, 440) is disposed in an anchor body (24, 124, 224, 424), and a screw cap body (58) is disposed about the outer attachment surface (30, 130, 230, 430) of the anchor body (24, 124, 224, 424). The screw cap body (58) engages the bone (22) of a person to support the dental implant assembly (20) and holds the core body (40, 140, 240, 340, 440) and the anchor body (24, 124, 224, 424) together.

China Patent Application Publication No. CN201026242
Inventor: Fengjian Zhou et al.
Published: Feb. 27, 2008

The utility model pertains to the oral medicine technical field, in particular to the dental implant technique. To reduce the troublesome process of the dental implant operation, the pile body and the base pile of present two-section dental implant are combined into an integrated dental implant. The integrated dental implant is divided into a root part and a coronal part, wherein the root part is provided with external screw threads and the root part can also be made into a branching root with 1-4 dental feet. The combined dental implant is made of nylon material or aramid fiber. Compared with prior two-section dental implant, the utility model has the advantage that the operation is more easy and convenient; the patient's pain is less; the operation is time saving and can be successful at one time; the price is lower, greatly reducing the period of treatment and the weight; and the load on the jaw bone is relieved. In use, the dental implant is very easy to hone into shape, so that the operation is more convenient and fast and the patient is more comfortable.

European Patent Application Publication EP2127612
Inventor: Daniel Baruc
Issued: Dec. 2, 2009

An abutment assembly device (115) comprises an abutment (122) for supporting a dental prosthesis (102). The abutment (122) includes a supporting surface (124) and an internal cavity with a rimmed opening, a hollow retainer wherein at least a portion of the retainer is flexible allowing that portion of the retainer to be inserted through the rimmed opening and snap into position retained by the rimmed opening. A screw for engaging the abutment assembly device (115) with an implant is provided, comprising a screw body and a screw head, wherein the screw head is wider than the screw body so that when the screw is inserted through the retainer and the retainer is retained by the rimmed opening, the screw head is retained by the retainer.

There are other dental endosteal implant abutments for replacing missing teeth. While these implants may be suitable for the purposes for which they were designed, they would not be as suitable for the purposes of the present invention as heretofore described.

SUMMARY OF THE PRESENT INVENTION

A primary object of the present invention is to provide an abutment system having a flexible inner core.

Another object of the present invention is to provide an abutment system wherein said flexible core is nested between an outer shell and an abutment base.

Still another object of the present invention is to provide an abutment system wherein said abutment base further comprises a post projecting from the bottom portion thereof for fixture to implant.

Yet another object of the present invention is to provide an abutment system wherein the restoration is solidly attached to the outer shell of the abutment.

Another object of the present invention is to provide an abutment system wherein said inner core is manufactured of a bio-compatible flexible material, like nylon.

Yet another object of the present invention is to provide an abutment system wherein said flexible material provides bio-compatibility and flexibility while maintaining the stringent requirements of implant abutments in terms of rigidity, bio-compatibility and bondability to restorations.

Still yet another object of the present invention is to provide an abutment system providing a similar feel as natural teeth while masticating.

Another object of the present invention is to provide an abutment system allowing for complete seating of restorationseven with a slight misfit.

Still another object of the present invention is to provide an abutment system that avoids premature occlusion when used next to natural teeth.

Yet another object of the present invention is to provide an abutment system wherein the flexibility provided by the flexible core enables implants to be connected directly to natural teeth.

Still yet another object of the present invention is to provide an abutment system that reduces the shocks of occlusional forces on the implants which contribute and encourage bone loss around the body of the implant that may ultimately result in the loss of integration.

Another object of the present invention is to provide an abutment assembly that is safe and durable in an oral environment.

Additional objects of the present invention will appear as the description proceeds.

The present invention overcomes the shortcomings of the prior art by providing a flexible core abutment system comprising a base member, a flexible inner core and an outer shell for receiving a restoration wherein the flexibility of the abutment simulates the elastic properties typically provided by the ligaments of natural teeth.

The foregoing and other objects and advantages will appear from the description to follow. In the description reference is made to the accompanying drawings, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which.

Figure 1:
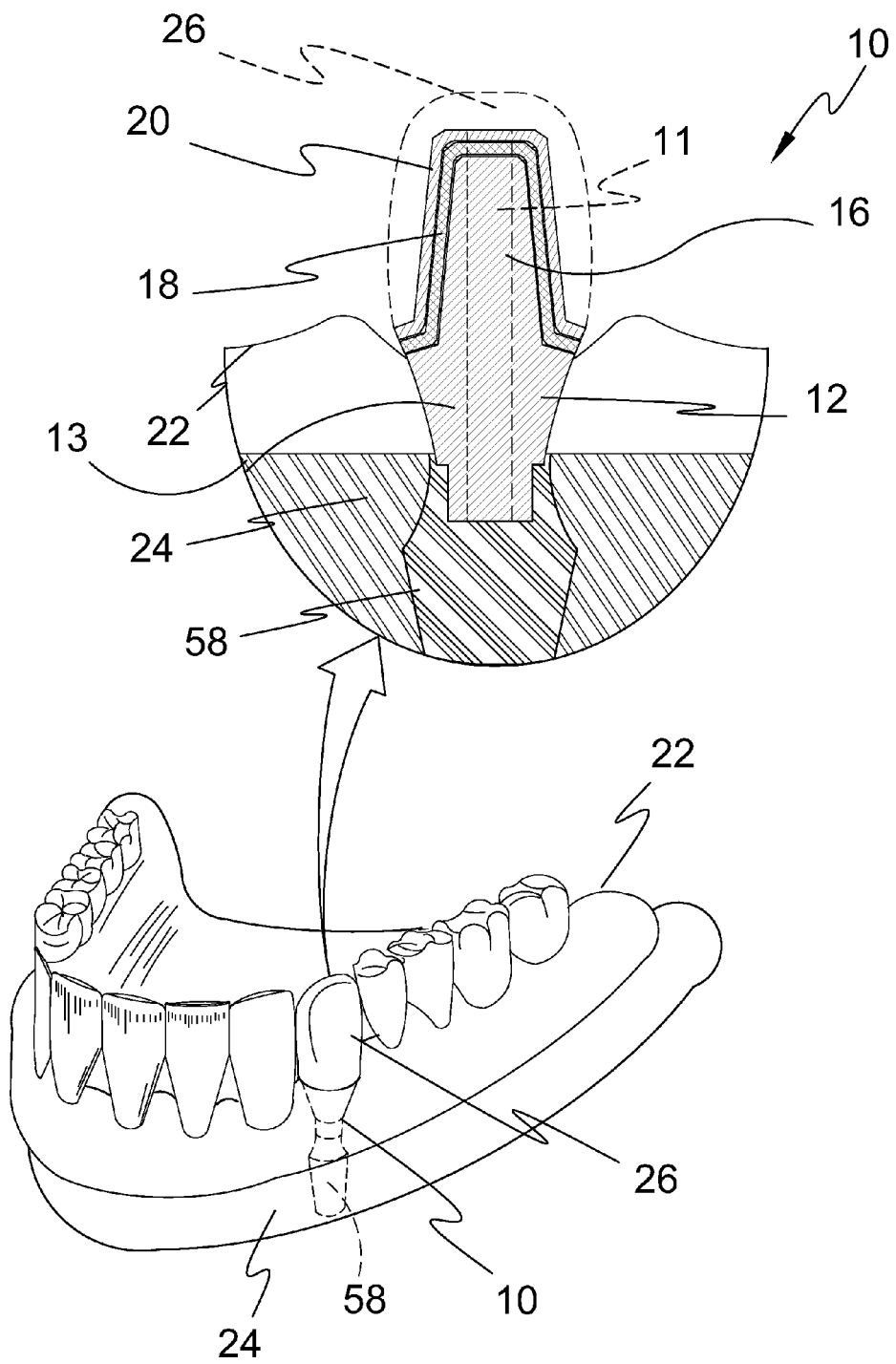
FIG. 1 is an illustrative view of the present invention in use.

Turning now descriptively to the drawings, in which similar reference characters denote similar elements throughout the several views, the figures illustrate the Flexible Core Abutment Assembly of the present invention. With regard to the reference numerals used, the following numbering is used throughout the various drawing figures.

10 Flexible Core Abutment Assembly of the present invention
    11 fastener aperture of 10
    12 abutment base
    13 body of 12
    14 anti-rotational shape
    16 head of 12
    18 flexible core
    20 outer shell
    22 gum line
    24 bone
    26 restoration
    28 titanium
    30 zirconium
    32 nylon or any other flexible material
    34 adhesive or mechanical retention
    36 base retaining flange
    38 flange of 18
    40 flange of 20
    42 exterior surface of 20
    44 interior surface of 20
    46 exterior surface of 18
    48 interior surface of 18
    50 outer shell cavity
    52 flexible core cavity
    54 base of 16
    56 access recesses
    58 implant post
    60 mechanical retention

DETAILED DESCRIPTION OF THE PREFERRED EMBODIMENT

The following discussion describes in detail one embodiment of the invention (and several variations of that embodiment). This discussion should not be construed, however, as limiting the invention to those particular embodiments, practitioners skilled in the art will recognize numerous other embodiments as well. For definition of the complete scope of the invention, the reader is directed to appended claims.

Referring to FIG. 1 shown is an illustrative view of the present invention in use. The present invention is a flexible core abutment assembly that is fastened to an implant post 58. The flexible core abutment assembly 10 comprises an abutment base 12 with a substantially flared body 13 an anti-rotational structure 14 projecting downwardly therefrom providing an anti-rotational feature of the abutment base and a head 16 projecting upwards therefrom, a flexible core 18 and an outer shell 20 with a fastener aperture 11 passing longitudinally through the assembly forming means for anchoring the abutment assembly 10 to the implant post 58. The restoration 26 is fixedly attached to outer shell 20.

Figure 2:
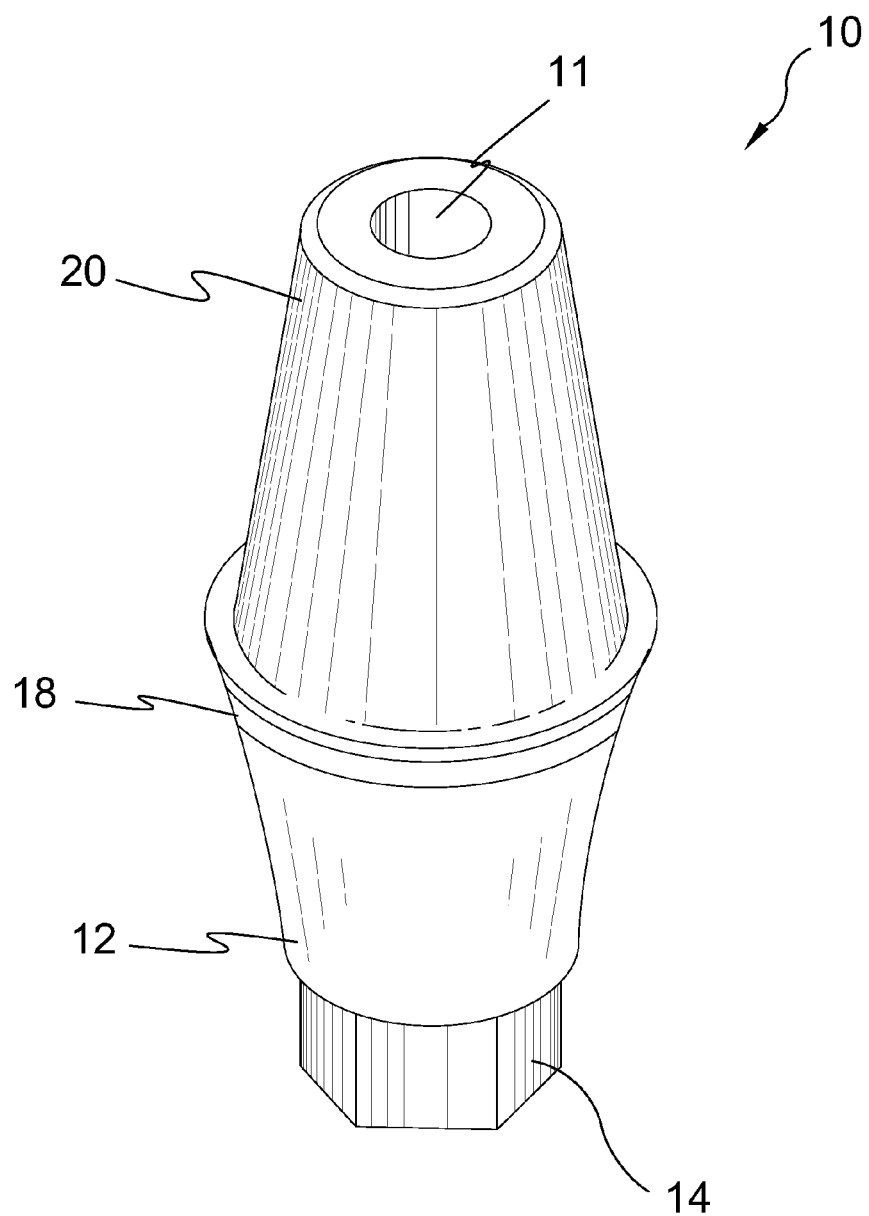
FIG. 2 is a perspective view of the present invention.

Referring now to FIG. 2, shown is a perspective view of the present invention. The components of the abutment assembly 10 comprise an outer shell 20, flexible core 18 and an abutment base 12 with an anti-rotational structure 14 projecting downward therefrom with a fastener aperture 11 passing longitudinally through said assembly.

Figure 3:
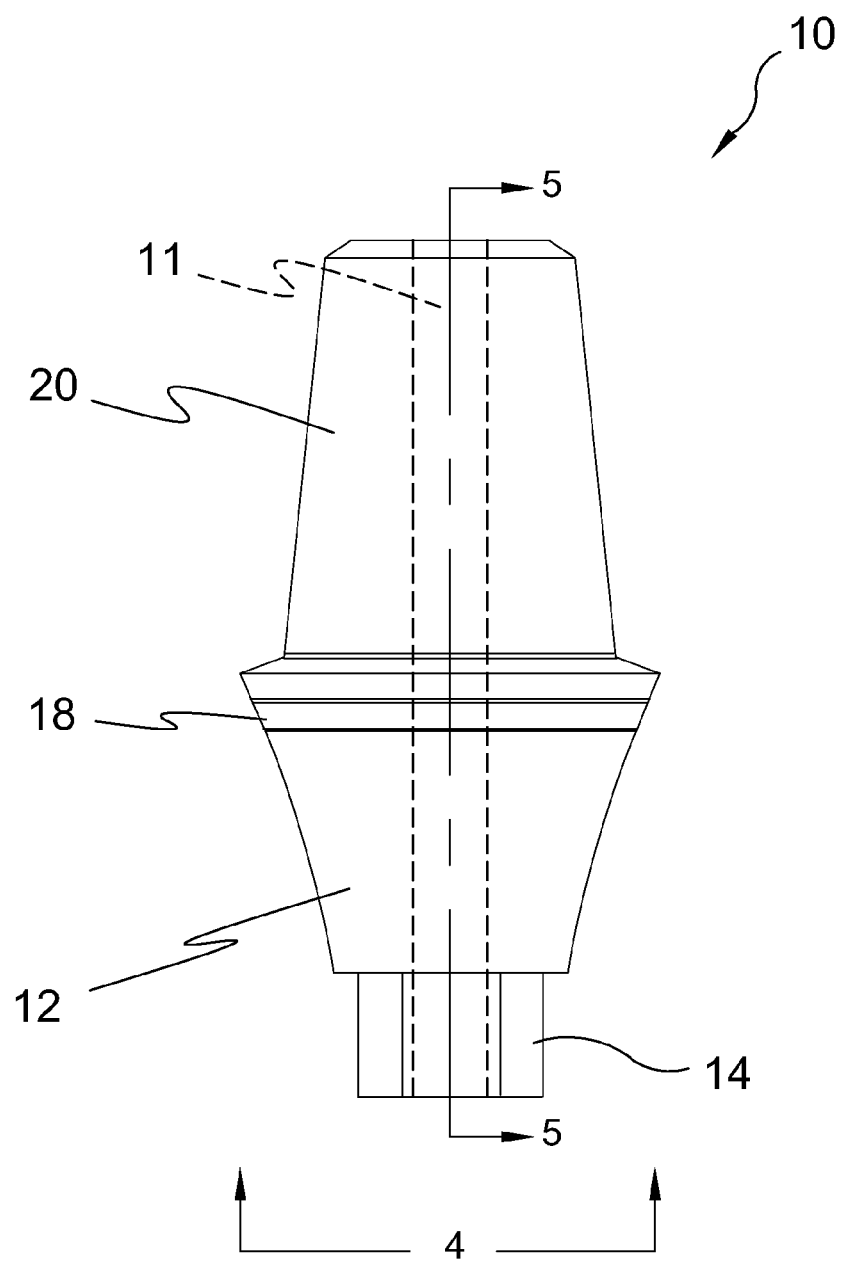
FIG. 3 is an orthographic view of the present invention.

Referring now to FIG. 3, shown is an orthographic view of the present invention. Illustrated is the assembled abutment assembly 10 comprising an outer shell 20, flexible core 18 and an abutment base 12 having a hex 14 shape providing an anti-rotational feature to said abutment assembly 10 when fixedly attached to the aforementioned implant post.

Figure 4:
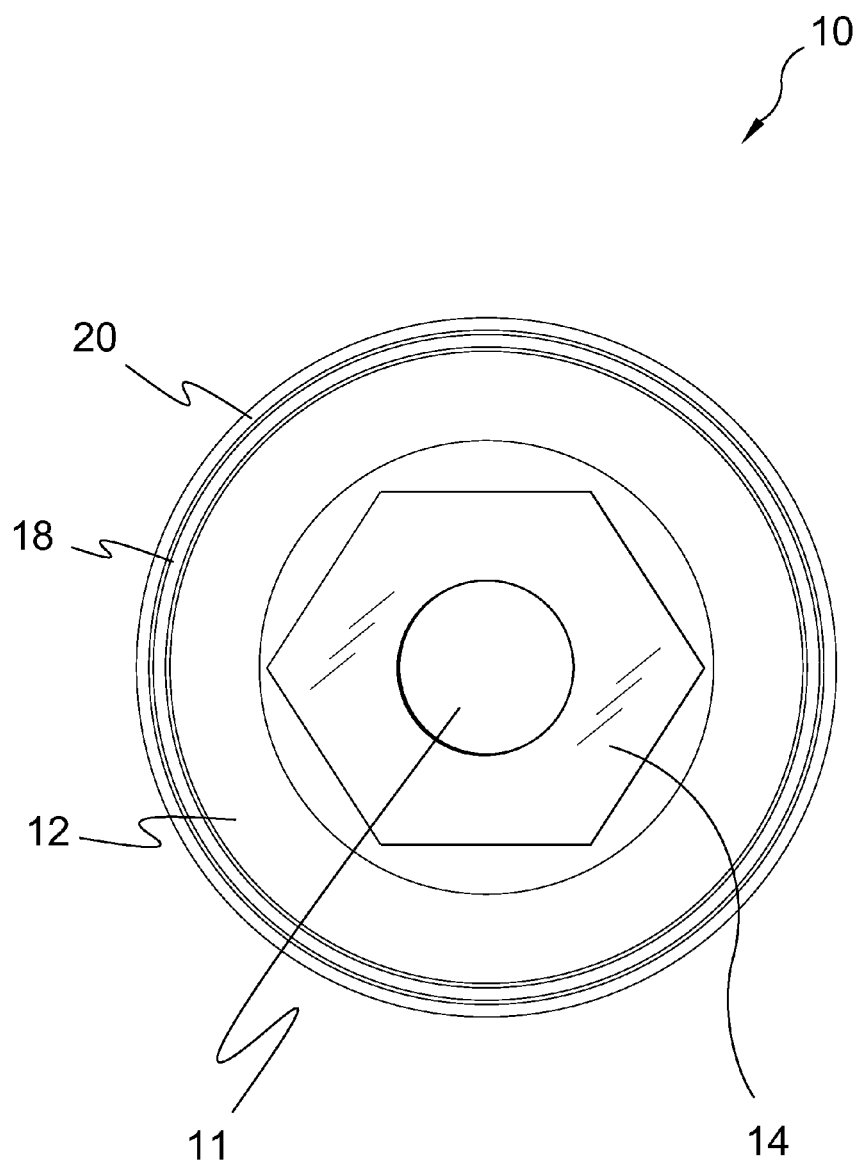
FIG. 4 is a bottom view of the present invention.

Referring to FIG. 4, shown is a bottom view of the present invention, taken from FIG. 3 as indicated. Illustrated is a bottom view of the abutment assembly 10 showing the outer shell 20, flexible core 18 and abutment base 12 with protruding abutment hex 14.

Figure 5:
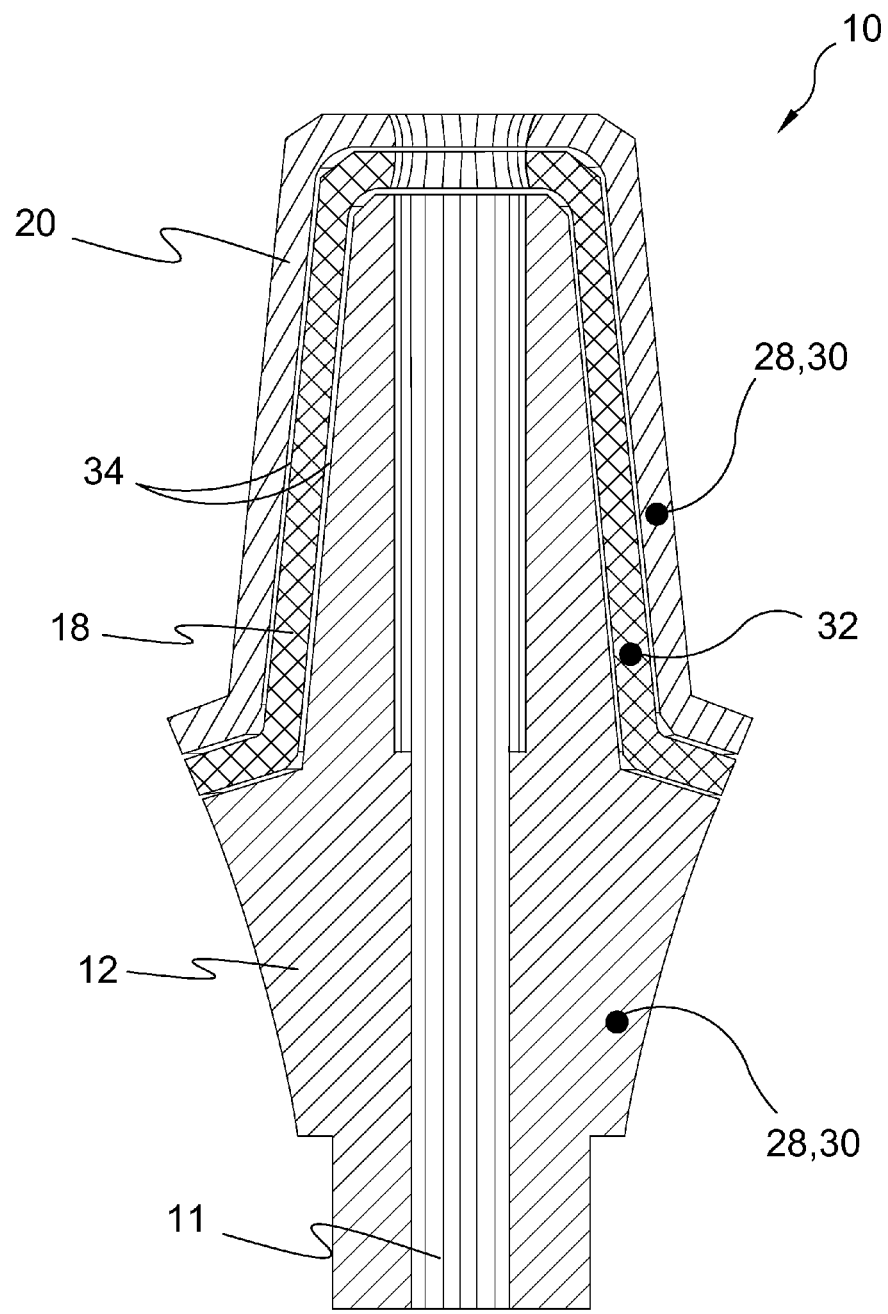
FIG. 5 is a cross sectional view of the present invention.

Referring to FIG. 5, shown is a cross sectional view, taken from FIG. 3 as indicated, of the abutment assembly 10. Depicted are the mating surfaces of the nested outer shell 20, flexible core 18 and abutment base 12 bonded together with an adhesive element 34. The flexible core 18 is preferably manufactured of a nylon material 32 to provide flexibility and the abutment base 12 and outer shell 20 are preferably manufactured of titanium 28 or zirconium 30.

Figure 6:
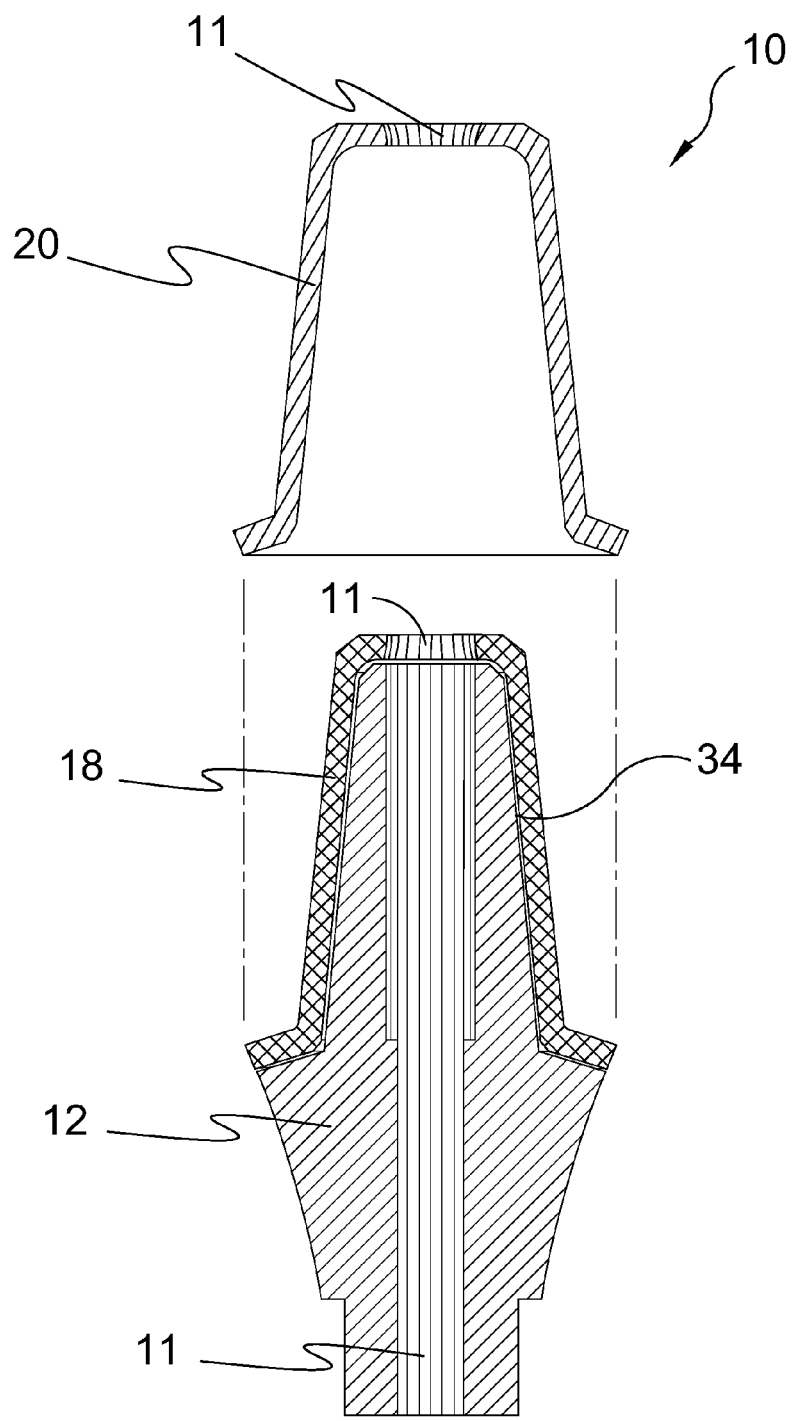
FIG. 6 is a partial exploded view of the present invention.

Referring to FIG. 6, shown is a partial exploded view of the abutment assembly 10. Shown is the flexible core 18 bonded to the abutment base 12 with an adhesive element 34 and the outer shell 20 prepared to be secured to the flexible core 18.

Figure 7:
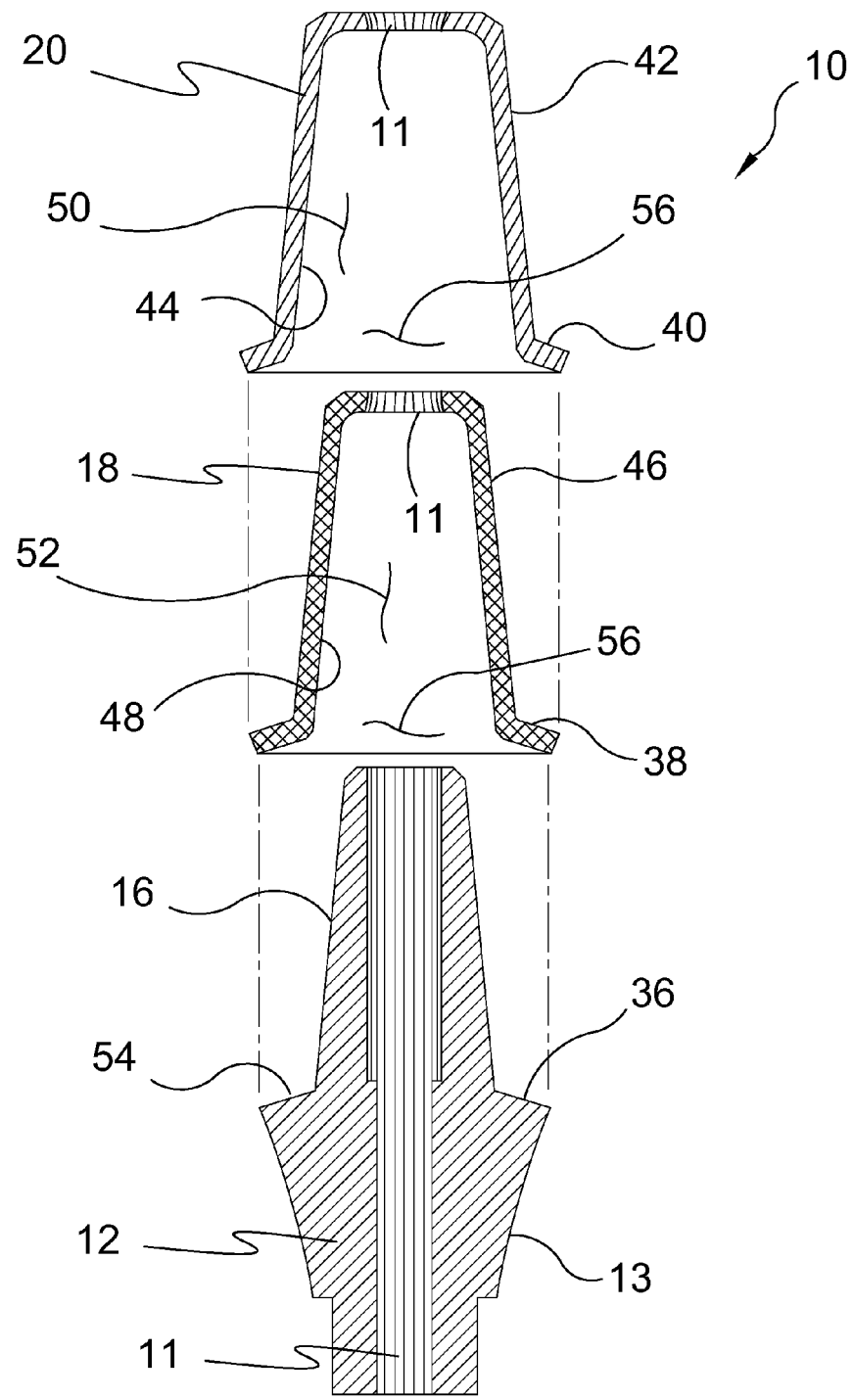
FIG. 7 is an exploded sectional view of the present invention.

Referring to FIG. 7, shown is an exploded sectional view of the abutment assembly 10 of the present invention. Shown is the abutment base 12 having a body 13 with an angular downwardly flared retaining platform 36 extending peripherally from the base 54 and the flexible core 18 with a flared peripheral angular flange 38 to be seated on the retaining platform 36. The outer shell 20 has a mating peripheral projection defining a corresponding shell flange 40 to be seated on said core flange 38. The outer shell 20 has an exterior surface 42 for receiving the restoration and an interior surface 44 defining a shell cavity 50 for receiving the exterior surface 46 of the flexible core 18. The core 18 has an exterior surface 46 corresponding with the interior surface 44 of said outer shell 20 and an interior surface 48 defining a core cavity 52 corresponding with the head 16 of said abutment base 12. Access recesses 56 are provided to allow entry into shell cavity 50 and core cavity 52. It will be understood that each of the elements described above, or two or more together may also find a useful application in other types of methods differing from the type described above.

Figure 8:
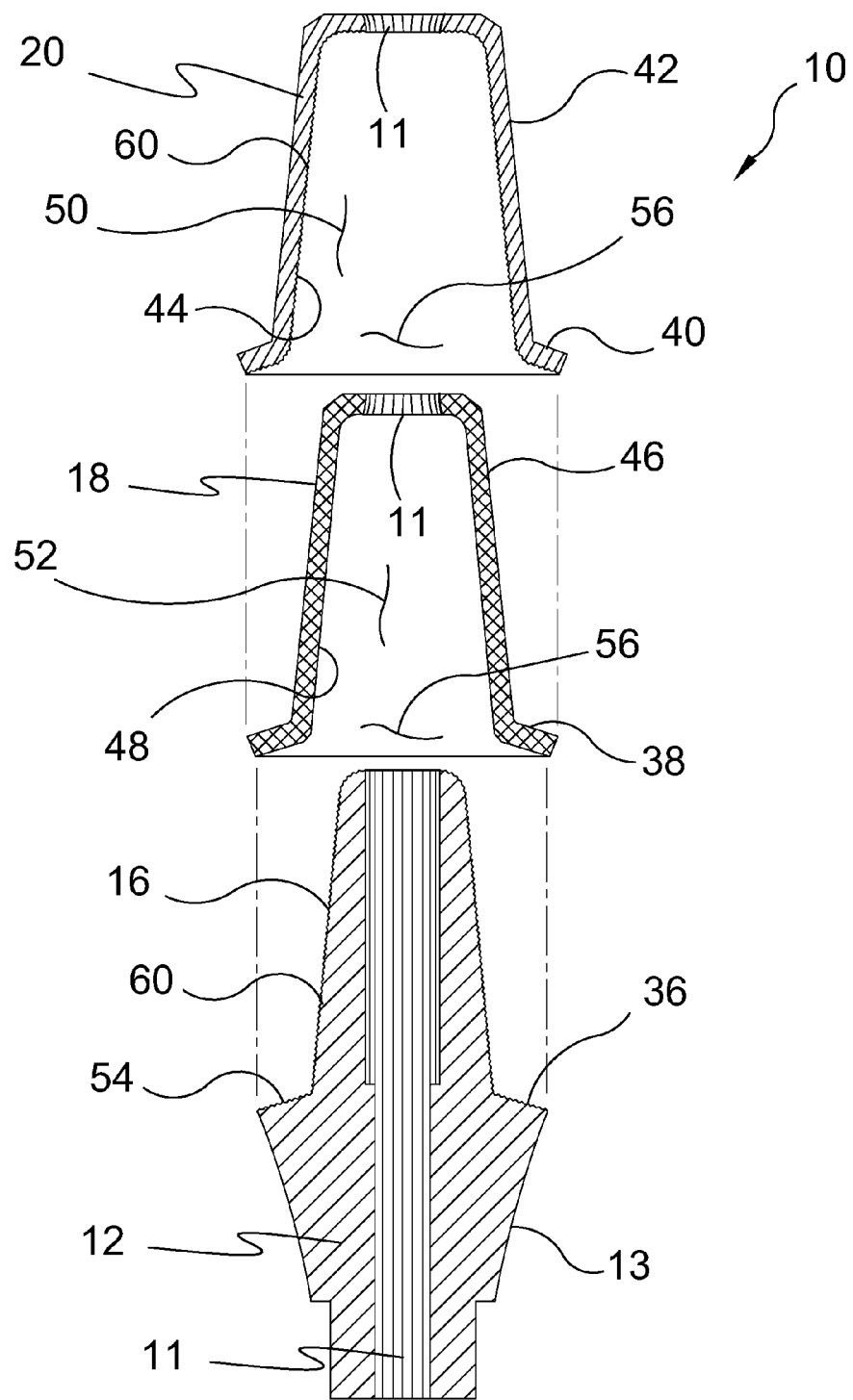
FIG. 8 is a sectional view of the present invention.

Referring to FIG. 8, shown is an exploded sectional view of the abutment assembly 10 of the present invention. The abutment base 12 having body 13 provides a mechanical retention element 60 in the form of a roughened or threaded surface covering head 16 through the downwardly angular flared retaining platform 36 extending peripherally along the base 54. The outer shell 20 has a mating peripheral projection defining a corresponding shell flange 40 to be seated on said core flange 38. The outer shell 20 has an exterior surface 42 for receiving the restoration and an interior surface 44 which also provides a mechanical retention element 60 in the form of a roughened or threaded surface defining a shell cavity 50 for receiving the exterior surface 46 of the core 18. The core 18 has an exterior surface 46 corresponding with the interior surface 44 of said outer shell 20 and an interior surface 48 defining a core cavity 52 corresponding with the head 16 of said abutment base 12. Access recesses 56 are provided to allow entry into shell cavity 50 and core cavity 52.

Figure 9:
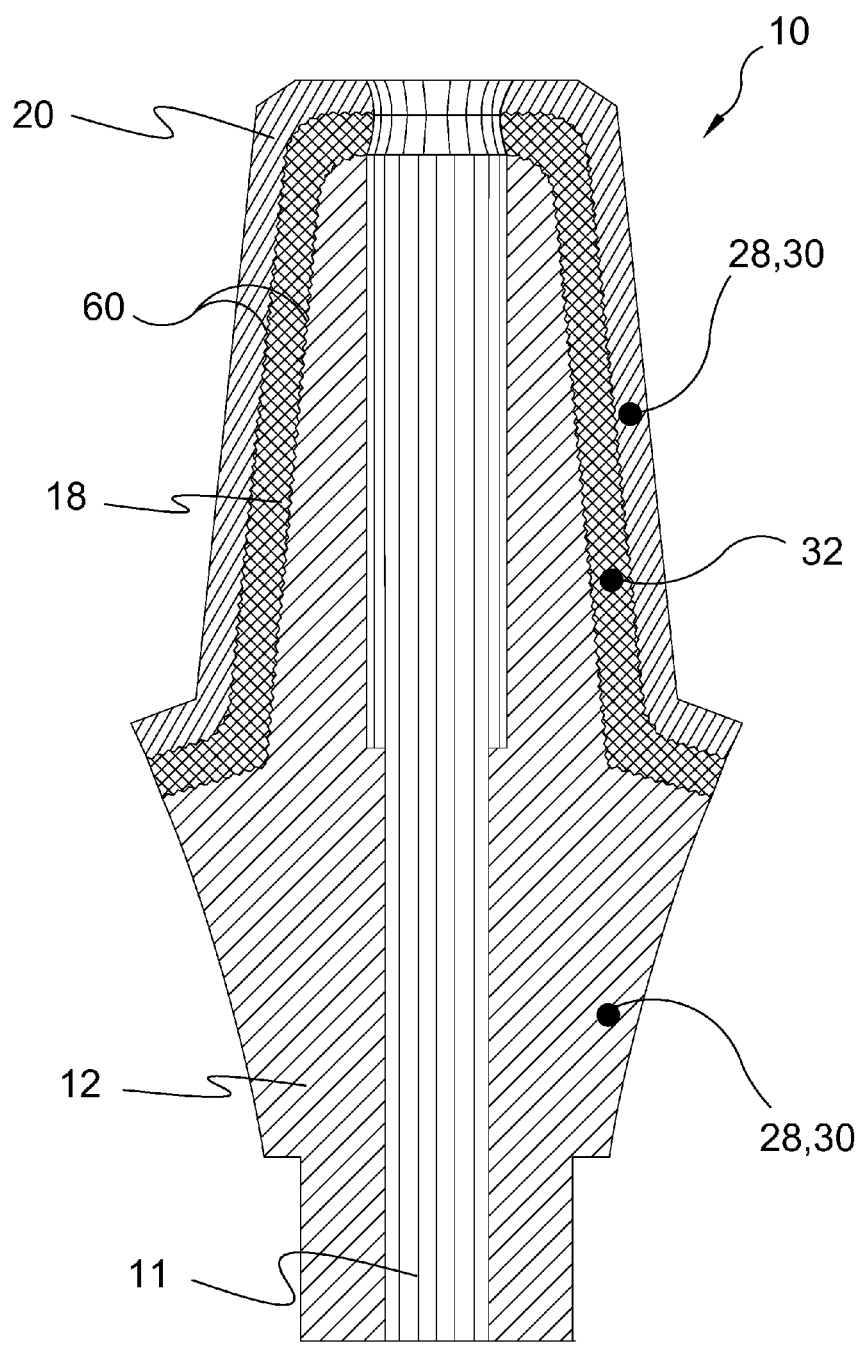
FIG. 9 is an assembled view of the present invention.

Referring to FIG. 9, shown is a sectional view of the abutment assembly 10. Depicted are the mating surfaces of the nested outer shell 20, flexible core 18 and abutment base 12 fixedly attached through micro mechanical locking or thread 60. The core 18 is preferably manufactured of a nylon material 32 to provide flexibility and the abutment base 12 and outer shell 20 are preferably manufactured of titanium 28 or zirconium 30.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is:

1. A flexible core abutment assembly providing a multi-layered abutment with a flexible core to provide versatility to the implantation and usage of restorations comprising:
   a) an abutment base member having a body;
   b) an outer shell with an interior surface and an exterior for receiving a restoration;
   c) a flexible middle core nested between said abutment base member and said outer shell;
   d) said abutment base member comprising an outwardly, downwardly and straight extending flange and a head emanating upwardly and tapering inwardly from said flange, wherein an upper side of said body of said base member terminates at a base of said head;
   e) wherein said outwardly extending flange of said abutment base member extends peripherally around said base of said head and projects angularly outward and downward to provide a retaining flange, outer faces of said head and flange intersecting at an unrounded juncture;
   f) said middle core having a middle core flange projecting outwardly, downwardly and straight from a bottom portion thereof;
   g) said outer shell having an outer shell flange projecting outwardly, downwardly and straight from a bottom portion thereof, outer faces of said outer shell and outer shell flange intersecting at an unrounded juncture, said outer shell and flexible middle core each being of uniform thickness throughout and being of substantially the same shape;

h) wherein said head is inserted into a cavity within said middle core until said middle core flange is seated upon said retaining flange and an outer surface of said head and upward facing outer surface of said retaining flange having roughened surfaces to provide mechanical retention of said middle core;

i) wherein an exterior surface of said middle core is inserted into a cavity within said outer shell until said outer shell flange is resting on said middle core flange;

j) wherein said head, said middle core and said outer shell are bound together with an adhesive element; and k) a fastener aperture extending passing longitudinally, and completely through said assembly.

2. The flexible core abutment assembly according to claim 1, further comprising an anti-rotational shape comprising a male hex projecting from a bottom portion of said body.

3. The flexible core abutment assembly according to claim 1, wherein the restoration is disposed on said outer shell.

4. The flexible core abutment assembly according to claim 3, wherein said assembly is implanted with said body residing below the gum line and a male hex fitted onto an implant that is integrated with bone.

5. The flexible core abutment assembly according to claim 1, wherein said flexible middle core is made of nylon material, and said outer shell is selected from the group consisting of titanium, zirconium or combination thereof.

6. The flexible core abutment assembly according to claim 1, wherein said base member and said outer shell are manufactured of titanium.

7. The flexible core abutment assembly according to claim 1, wherein said abutment base member and said outer shell are manufactured of zirconium.

8. The flexible core abutment assembly according to claim 1, wherein said abutment base member and said outer shell are comprised of a combination of titanium and zirconium.

9. The flexible core abutment assembly according to claim 1, whereby said flexible middle core is made of a material which performs the function of the natural ligaments by providing cushioning when restoration is subjected to occlusal loads thereby conveying similar behavior to natural teeth when used next to natural teeth.

10. The flexible core abutment assembly according to claim 1, wherein a material selected for use as said flexible middle core has compression characteristics which provides a similar behavior as natural teeth.

\* \* \* \* \*